(12) United States Patent
Kuesel

(10) Patent No.: US 10,189,649 B2
(45) Date of Patent: Jan. 29, 2019

(54) CONVEYING SYSTEM

(71) Applicant: Phoenix Conveyor Belt Systems GmbH, Bad Blankenburg (DE)

(72) Inventor: Bernd Kuesel, Hamburg (DE)

(73) Assignee: Phoenix Conveyor Belt Systems GmbH, Bad Blankenburg (DE)

( * ) Notice: Subject to any disclaimer, the term of this patent is extended or adjusted under 35 U.S.C. 154(b) by 0 days.

(21) Appl. No.: 15/882,856

(22) Filed: Jan. 29, 2018

(65) Prior Publication Data

US 2018/0148266 A1 May 31, 2018

Related U.S. Application Data

(63) Continuation of application No. PCT/EP2016/059022, filed on Apr. 22, 2016.

(30) Foreign Application Priority Data

Jul. 27, 2015 (DE) .......... 10 2015 214 159

(51) Int. Cl.
| | |
|---|---|
| *B65G 43/02* | (2006.01) |
| *B65G 43/04* | (2006.01) |
| *B65G 15/64* | (2006.01) |
| *B65G 45/16* | (2006.01) |
| *B65G 45/14* | (2006.01) |

(Continued)

(52) U.S. Cl.
CPC ............. *B65G 43/02* (2013.01); *B65G 15/64* (2013.01); *B65G 45/14* (2013.01); *B65G 47/44* (2013.01); *G01N 23/04* (2013.01); *B65G 43/04* (2013.01); *B65G 45/16* (2013.01); *B65G 2203/0275* (2013.01); *B65G 2203/042* (2013.01)

(58) Field of Classification Search
CPC ........ B65G 43/02; B65G 43/04; B65G 45/16; B65G 15/64
USPC ............. 198/810.01, 810.02, 810.03, 810.04
See application file for complete search history.

(56) References Cited

U.S. PATENT DOCUMENTS

| | | | | |
|---|---|---|---|---|
| 6,032,787 A | * | 3/2000 | Kellis | .............. B65G 43/02 198/502.1 |
| 6,781,515 B2 | * | 8/2004 | Kuzik | .............. B65G 43/02 198/810.02 |
| 6,831,566 B1 | | 12/2004 | Kuesel | |

(Continued)

FOREIGN PATENT DOCUMENTS

| | | |
|---|---|---|
| CN | 101825584 A | 9/2010 |
| DE | 3517314 A1 | 1/1986 |

(Continued)

OTHER PUBLICATIONS

International Search Report dated Jul. 18, 2016 of international application PCT/EP2016/059022.

(Continued)

*Primary Examiner* — Douglas A Hess
(74) *Attorney, Agent, or Firm* — Walter Ottesen, P.A.

(57) ABSTRACT

The invention is directed to a conveying system which includes an endless conveyor belt and at least one non-destructive inspection device for inspecting the conveyor belt. The inspection device generates and outputs a result of the inspection. The conveying system has at least one adjustable conveying system element and at least one control unit which adjusts the adjustable conveying system element in dependence on the result of the inspection.

8 Claims, 1 Drawing Sheet

(51) Int. Cl.
*B65G 47/44* (2006.01)
*G01N 23/04* (2018.01)

(56) References Cited

U.S. PATENT DOCUMENTS

| | | | | |
|---|---|---|---|---|
| 7,427,767 | B2 * | 9/2008 | Kemp | B65G 43/02 |
| | | | | 198/502.1 |
| 7,673,740 | B2 * | 3/2010 | Kusel | B65G 43/02 |
| | | | | 198/810.02 |
| 7,894,934 | B2 * | 2/2011 | Wallace | B65G 43/00 |
| | | | | 198/341.01 |
| 8,149,989 | B2 * | 4/2012 | Schnell | B65G 43/02 |
| | | | | 378/58 |
| 8,607,964 | B2 | 12/2013 | Kheifets | |
| 8,807,331 | B2 | 8/2014 | Beltman et al. | |
| 8,891,730 | B2 * | 11/2014 | Kuesel | B65G 15/36 |
| | | | | 378/58 |
| 8,983,027 | B2 | 3/2015 | Kuesel | |
| 9,227,793 | B2 * | 1/2016 | Rathmann | B65G 43/02 |
| 9,811,809 | B2 * | 11/2017 | Sakuragi | B65G 43/02 |
| 2012/0031736 | A1 | 2/2012 | Swinderman et al. | |
| 2013/0015354 | A1 * | 1/2013 | Diamond | |
| 2013/0136816 | A1 | 5/2013 | Kuesel | |
| 2014/0131176 | A1 * | 5/2014 | Minkin | |

FOREIGN PATENT DOCUMENTS

| | | |
|---|---|---|
| DE | 19929099 A1 | 12/2000 |
| DE | 10140920 A1 | 5/2002 |
| DE | 102004014084 A1 | 10/2004 |
| KR | 20150076018 A | 7/2015 |

OTHER PUBLICATIONS

Examination report No. 1 for standard patent application of the Australian Intellectual Property Office dated Jul. 18, 2018 in corresponding Australian patent application 2016299453.

* cited by examiner

CONVEYING SYSTEM

CROSS REFERENCE TO RELATED APPLICATIONS

This application is a continuation application of international patent application PCT/EP2016/059022, filed Apr. 22, 2016, designating the United States and claiming priority from German application 10 2015 214 159.4, filed Jul. 27, 2015, and the entire content of both applications is incorporated herein by reference.

FIELD OF THE INVENTION

The invention relates to a conveying system and to an inspection device utilized in such a conveying system.

BACKGROUND OF THE INVENTION

Conveying systems may represent very expensive investments, in terms of both procurement and operation. In particular, if a conveying system does not operate, for example in a mine, this can have the effect that the entire mining facility does not operate, including transporting the extracted material away. This can cause enormous costs, in particular due to lost production.

For this reason, monitoring systems for conveyor belts of conveying systems are known so that damage and the like can be detected as early as possible, before the damage puts the conveyor belt, and consequently the conveying system, out of operation. It is for example intended that, when damage is detected, a warning is generated, preferably also comprising locating the damage, so that the conveyor belt can be stopped and the damage can be rectified by personnel.

Such a device for the non-destructive inspection of a conveyor belt is described in DE 35 17 314 A1 which is incorporated herein by reference. There, the monitoring, inspecting or checking of conveyor belts is performed by means of x-radiation, which can pass through a conveyor belt. The x-radiation that has passed through the conveyor belt is captured and produces a visible image of the interior of the conveyor belt on a fluorescent screen, so that damage within the material of the conveyor belt can be detected. This visible image can be visually examined by personnel or recorded by a video camera, in order to be visually examined later. It is consequently possible not only for damage to be detected by personnel but also for possible conclusions of such damage to be drawn by personnel and also to be initiated or implemented.

US 2013/0136816 and U.S. Pat. No. 8,983,027 also relate to devices for the non-destructive inspection of conveyor belts by x-radiation and are incorporated herein by reference. In those documents, however, the evaluation of the measurement data takes place in each case by means of a process computer or by means of image processing software, so that there is no need for the evaluation of images by personnel of the conveying system. In both cases, automatic error messages can be generated if relevant damage is detected by the process computer or the image processing software. Personnel can respond to this error message, in that possible conclusions in this respect can be drawn by personnel and also can be initiated or implemented.

SUMMARY OF THE INVENTION

It is an object of the invention to provide a conveying system of the type described above such that it is possible to respond more quickly, safely and/or in a more targeted manner to detected damage to the conveyor belt.

The object is achieved according to the invention by a conveying system which includes an endless conveyor belt and at least one non-destructive inspection device for inspecting the conveyor belt, the inspection device being able to generate and output a result of the inspection. The inspection device can carry out the non-destructive inspection for example by means of x-radiation, by means of laser detection or laser scanning and also opto-electronically or magneto-inductively. The result of the inspection may be the recorded data of the inspection device, which are to be further processed and evaluated elsewhere, and also a result of an evaluation, which can be performed by the inspection device itself.

The conveying system includes at least one adjustable conveying system element and at least one control unit, which can adjust the adjustable conveying system element in dependence on the result of the inspection. The control unit may be a separate unit, which is connected in signal-transmitting relative to the inspection device, or the control unit may be a component part of the inspection device.

An adjustable conveying system element should be understood as meaning any device of the conveying system which has at least one actuator or drive that can be controlled in an open-loop or closed-loop manner. This actuator or drive may already be present as a result of the actual function of the conveying system element and be additionally adjusted in response to the inspection result within the scope of the present invention, or the actuator or drive may be additionally provided, in order to make the adjustability of the conveying system element possible within the scope of the present invention.

The present invention is based on the idea of automating a response to an inspection result of the inspection system instead of having it carried out by personnel. This is intended to avoid human error. It is also intended that defined responses to defined inspection results, which may have previously been stored by the personnel in the control unit, can be carried out automatically. These inspection results and/or responses may also be changed by the personnel or else include further interrelationships, such as for example the dependence on further results such as for example variations over time or points in time.

In other words, it is intended to make it possible to inspect the state of the conveyor belt permanently and in real time and to automatically derive responses from the detection of changes in the state of the conveyor belt. This detection is intended to be linked with other parts of the system and communicated with them. For this purpose, actions by the other parts of the system are intended to be derived from the detection of the change in the state of the conveyor belt and carried out by them. Consequently, the present invention in other words also relates to an interconnection of a monitoring system of a conveying system with its individual system parts.

According to one aspect of the present invention, the adjustable conveying system element is a drive drum. In this way, the conveying system can be stopped automatically if an imminent fault or imminent damage is detected, or even a tearing of the conveyor belt. Immediate abrupt stopping of the systems may take place in the event of an emergency or else the conveyor belt may be stopped in a controlled manner, if there is sufficient time for this, which may be less harmful to the conveyor belt, in order not to make the damage any worse. The drive output of the conveyor belt may also be reduced by way of the drive drum if the damage allows the conveying system to continue operating, but to do so with reduced output, in order not to make the damage any worse. This allows production to be maintained for a certain time, in order for example to prepare repair measures at the same time and to minimize the subsequent downtime.

According to a further aspect of the present invention, the adjustable conveying system element is a deflection drum. In this way, skewed running of the conveyor belt can be detected by the inspection device and corrected by an adjustment of the deflection drum.

According to a further aspect of the present invention, the adjustable conveying system element is a stripper. A stripper serves for removing contaminants from the surface of the conveyor belt, for example, the material conveyed, and is therefore usually arranged just after the discharge point on the lower strand. So if excessive soiling left on the surface of the conveyor belt is detected by the inspection device, the distance between the stripper edge and the surface of the conveyor belt can be adjusted to be smaller, in order to improve the cleaning effect of the stripper.

According to a further aspect of the present invention, the adjustable conveying system element is a chute. If, for example, longitudinal streaks in the edge region of the upper side of the conveyor belt are detected by the inspection device, the corresponding chute strip can thus be adjusted in order to avoid this contact.

According to a further aspect of the present invention, the control unit is set up to adjust at least the adjustable conveying system element with a time delay with respect to the result of the inspection. In this way, for example, stopping of the conveying system can take place with a time delay in dependence on a detected fault of the conveyor belt, so that a servicing stop or a stop to repair the conveyor belt that is required on the basis of the inspection results can be made to coincide with a known and in any case planned servicing stop of another part of the system, such as for example motors or gear mechanisms. Consequently, at least two parts of the system can be serviced or repaired at the same time instead of having two stops, whereby the downtimes of the conveying system, and consequently the resultant losses of production, can be reduced.

According to a further aspect of the present invention, the control unit and/or the inspection device can classify the result of the inspection and the control unit can adjust the adjustable conveying system element in dependence on the classification of the result of the inspection. In this way, the intelligence of the present invention can be arranged in the control device or in the inspection device, from which then instructions for action are sent to the other parts of the system. The classification of the inspection results may take place for example on the basis of importance or urgency, so that, as a response to this, an emergency stop signal, a warning message or an instruction for action to a drive or a number of drives of an adjustable element or of a number of adjustable elements can be effected.

According to a further aspect of the present invention, the non-destructive inspection device can carry out the inspection by means of high-energy radiation, which can be emitted to the surface of the conveyor belt, can pass through the material of the conveyor belt and can be contactlessly detected on the opposite side of the conveyor belt. This may for example be x-rays. Such a system is known for example from U.S. Pat. No. 8,983,027 which is incorporated herein by reference. In this way, a non-destructive inspection of the conveyor belt can also be made possible in its interior.

According to a further aspect of the present invention, the control unit is a component part of the inspection device. In this way, the signal transmission of the inspection result can take place more quickly, so that the response to it can also be determined and initiated more quickly. Furthermore, it is possible to dispense with a further unit of the conveying system, which can make the implementation of the invention easier and more affordable and increase acceptance on the part of the system operator.

The present invention also relates to an inspection device for use in the case of a conveying system as described above.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
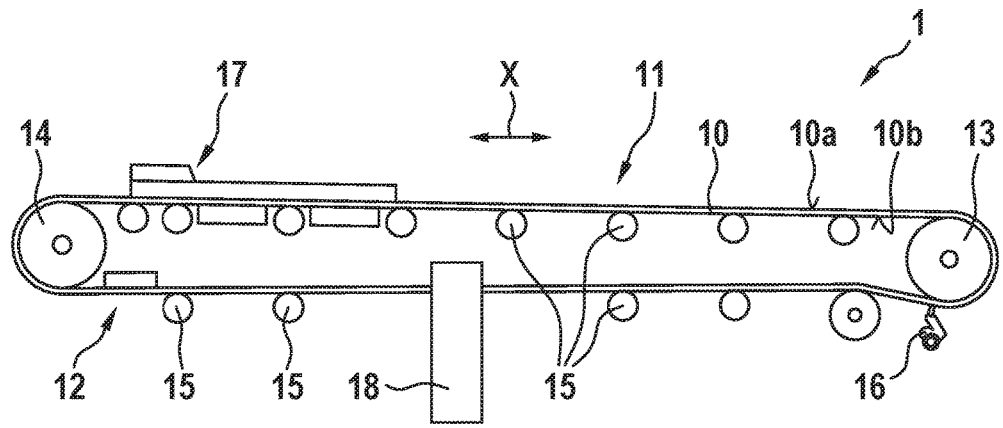
FIG. 1 shows a schematic side-elevation view of a conveying system according to the invention; and, FIG. 2 shows a schematic block diagram of the interaction of various conveying system elements of the conveying system according to the invention.

FIG. 1 shows a schematic side-elevation view of a conveying system 1 according to the invention. The conveying system 1 runs substantially in a longitudinal direction X, which may therefore also be referred to as the conveying direction X. The conveying system 1 may also be referred to as the transporting belt system 1.

The conveying system 1 has an endless conveyor belt 10, which may also be referred to as a transporting belt 10. The conveyor belt 10 has an upper side 10a, on which the material conveyed (not represented) can be transported. The material conveyed may be in particular loose bulk material, such as for example products extracted from a mine, but also other bulk materials, such as for example sand, gravel, foodstuffs, chemicals, et cetera, may be transported.

Opposite from the upper side 10a, the conveyor belt 10 has an underside 10b, with which the conveyor belt 10 rests on a drive drum 13, a deflection drum 14 and also a multiplicity of carrying rollers 15 and by way of which the conveyor belt 10 can be driven and guided. The upper running path of the conveyor belt 10, in which the material conveyed can be transported, may be referred to as the upper strand 11 and the lower running path may be referred to as the lower strand 12. In the region of the upper strand 11, a chute 17 is provided at the discharge point of the material conveyed onto the conveyor belt 10 near the deflection drum 14, in order to feed the material conveyed onto the conveyor belt 10 in a defined manner. In the region of the lower strand 12, a stripper 16 is provided shortly after the drive drum 13 in the conveying direction x, in order to clean the upper side 10a of the conveyor belt 10 of contaminants as soon as possible after the discharge of the material conveyed.

Arranged beyond the stripper 16 in the conveying direction X is an inspection device 18 in the form of an x-ray device 18, which may also be referred to as a monitoring device 18. The inspection device 18 is configured to inspect the conveyor belt 10 outwardly and inwardly for its condition when it has been cleaned by the stripper 16 and is free of material conveyed. This is intended to include detecting and evaluating every cubic millimeter of the conveyor belt 10 or of its material. This can take place by means of a control device 19, which may also be referred to as a process computer 19. The control unit 19 is preferably a component part of the inspection device 18.

Figure 2:
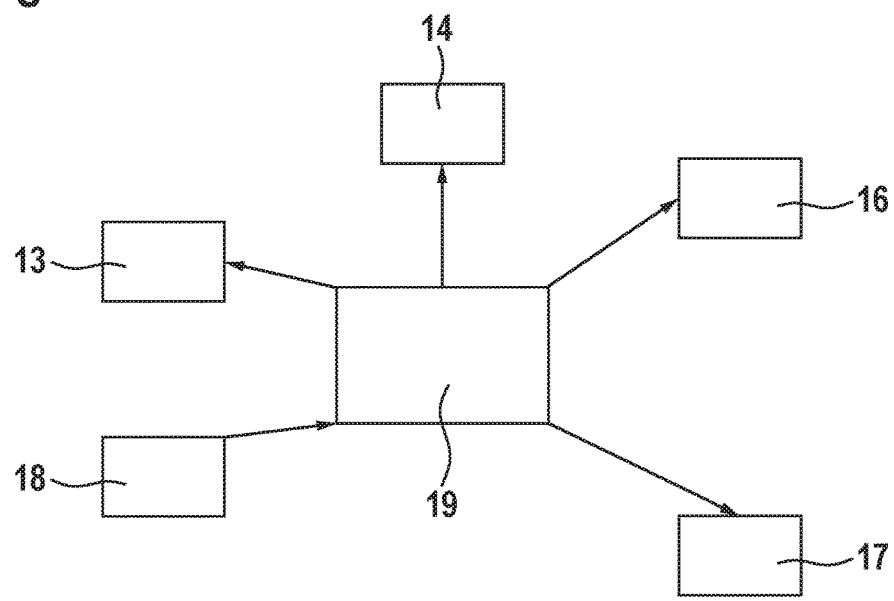

FIG. 2 shows a schematic block diagram of the interaction of various conveying system elements 13, 14, 16, 17 of the conveying system 10 according to the invention. According to the invention, the aforementioned elements of the conveying system 10, such as the drive drum 13, the deflection drum 14, the stripper 16 and the chute 17, are configured to be adjustable. This means that these conveying system elements 13, 14, 16, 17 each have additional actuators, which can be controlled by the control unit 19, or that the existing actuators can, in addition to their usual function, be controlled by the control unit 19.

If, consequently, during the inspection of the conveyor belt 10 by the inspection device 18, a deviation from the prescribed normal state is detected, this inspection result is passed on to the control unit 19. The response to the inspection result is then determined by the control unit 19 and the corresponding instructions are given to the corresponding adjustable conveying system elements 13, 14, 16, 17. This may, for example, be a reduction of the drive output of the drive drum 13, a skewed running correction of the deflection drum 14, a correction of the chute strips of the chute 17 or a distance correction of the stripper 16. There may also be an emergency stop of the conveying system 10. Furthermore, the conveying system 10 may be stopped in order to allow personnel to rectify damage to the conveyor belt 10 or to allow personnel to carry out inspection. This stopping of the conveyor belt 10 may also take place automatically with a time delay and at the same time as an in any case planned servicing stop of the conveying system 10, in order to minimize the time for which the conveying system 10 is stopped, and consequently non-conveying times.

It is understood that the foregoing description is that of the preferred embodiments of the invention and that various changes and modifications may be made thereto without departing from the spirit and scope of the invention as defined in the appended claims.

LIST OF REFERENCE SIGNS

Part of the Description

X Longitudinal direction, conveying direction
1 Conveying system, transporting belt system
10 Conveyor belt, transporting belt
10a Upper side of the conveyor belt 10
10b Underside of the conveyor belt 10
11 Upper strand
12 Lower strand
13 (Adjustable) drive drum
14 (Adjustable) deflection drum
15 Carrying rollers
16 (Adjustable) stripper
17 (Adjustable) chute
18 Inspection device, monitoring device
19 Control unit, process computer

What is claimed is:

1. A conveying system for conveying material, the conveying system comprising:
   a continuous conveyor belt having upper and lower strands;
   a non-destructive inspection device mounted at said lower strand and being configured to inspect said continuous conveyor belt and to generate and output a result of an inspection of said conveyor belt;
   an adjustable drive drum element operatively connected to said conveyor belt;
   an adjustable deflection drum element operatively connected to said conveyor belt;
   an adjustable stripper element mounted at said lower strand ahead of said non-destructive inspection device so as to permit removal of any residual quantities of said material before said lower strand reaches said inspection device; and,
   a control unit for adjusting any one of said elements in dependence upon said result of said inspection.

2. The conveying system of claim 1, wherein said stripper element is adjustable in elevation with respect to said lower strand to improve clearing of said conveyor belt.

3. The conveying system of claim 1, wherein said control unit is configured so as to cause at least one of said adjustable conveying system elements to be adjusted with a time delay relative to said result of said inspection.

4. The conveying system of claim 1, wherein at least one of said control unit and said inspection device is configured to classify said result of said inspection and said control unit is further configured to adjust said adjustable conveying system element in dependence upon the classification of said result of said inspection.

5. The conveying system of claim 1, wherein said conveyor belt has an upper or outer surface and a lower or inner surface; and, said non-destructive inspection device is configured to carry out said inspection with high-energy radiation transmitted to said upper or outer surface of said continuous conveyor belt so as to pass through the material thereof and be detected contactlessly at said lower or inner surface of said continuous conveyor belt.

6. The conveying system of claim 1, wherein said control unit is part of said inspection device.

7. A conveying system for conveying material, the conveying system comprising:
   a continuous conveyor belt having upper and lower strands;
   a non-destructive inspection device mounted at said lower strand and being configured to inspect said continuous conveyor belt and to generate and output a result of an inspection of said conveyor belt;
   an adjustable drive drum element operatively connected to said conveyor belt;
   an adjustable deflection drum element operatively connected to said conveyor belt;
   an adjustable stripper element mounted at said lower strand ahead of said non-destructive inspection device so as to permit removal of any residual quantities of said material before said lower strand reaches said inspection device;
   an adjustable chute element mounted at said upper strand for discharging said material on to said upper strand; and,
   a control unit for adjusting any one of said elements in dependence upon said result of said inspection.

8. The conveying system of claim 7, wherein said adjustable chute element can come into contact with an edge region of said continuous conveyor belt and cause streaks therein detected by said inspection device; and, said control unit is configured to respond to the detection of said streaks by said inspection device to adjust said chute element to avoid said contact.

* * * * *